US007110821B1

(12) United States Patent
Ross (10) Patent No.: US 7,110,821 B1
(45) Date of Patent: Sep. 19, 2006

(54) CHANNEL INTERACTION CANCELLATION WITHIN A MULTICHANNEL NEURAL STIMULATION SYSTEM

(75) Inventor: Richard C. Ross, Westlake Village, CA (US)

(73) Assignee: Advanced Bionics Corporation, Valencia, CA (US)

( * ) Notice: Subject to any disclaimer, the term of this patent is extended or adjusted under 35 U.S.C. 154(b) by 627 days.

(21) Appl. No.: 10/192,987

(22) Filed: Jul. 10, 2002

(51) Int. Cl.
*A61N 1/36* (2006.01)

(52) U.S. Cl. ............................... 607/57; 607/2; 607/62; 600/559

(58) Field of Classification Search .................... 607/2, 607/53–57, 39–41, 46, 68, 8, 62; 600/554, 600/559; 128/901
See application file for complete search history.

(56) References Cited

U.S. PATENT DOCUMENTS

| | | | |
|---|---|---|---|
| 4,400,590 A | 8/1983 | Michelson | |
| 4,408,608 A | 10/1983 | Daly et al. | |
| 4,648,403 A * | 3/1987 | Van Compernolle | 607/57 |
| 4,819,647 A | 4/1989 | Byers et al. | |
| 5,324,316 A | 6/1994 | Schulman et al. | |
| 5,571,148 A | 11/1996 | Loeb et al. | |
| 5,603,726 A | 2/1997 | Schulman et al. | |
| 5,824,022 A | 10/1998 | Zilberman et al. | |
| 6,129,753 A | 10/2000 | Kuzma | |
| 6,175,767 B1 | 1/2001 | Doyle, Sr. | |
| 6,308,101 B1 | 10/2001 | Faltys et al. | |
| 6,516,227 B1 | 2/2003 | Meadows et al. | |

FOREIGN PATENT DOCUMENTS

WO   WO-02/09808 A1   2/2002

OTHER PUBLICATIONS

Stickney, G. S., et al., (2001) "Electrode Interaction and Speech Intelligibility in Multichannel Cochlear Implants". Poster Presentation, Presented at the 2001 Conference on Implantable Auditory Prostheses, Pacific Grove, CA.
Stickney, G. S., et al., (2000) "Channel Interaction and Speech Processing Strategies for Cochlear Implants". Poster Presentation, Presented at the 104th Meeting of the Acoustical Society 2000.
Boëx, et al., (1999) "Electrode Interaction in Clarion Subjects", University Hospitals, Geneva, Switzerland. Poster Presentation, Presented at the 1999 Conference on Implantable Auditory Prostheses, Asilomar, CA.

* cited by examiner

*Primary Examiner*—Kennedy Schaetzle
(74) *Attorney, Agent, or Firm*—Bryant R. Gold; Victoria A. Poissant (57) ABSTRACT

A way of reducing channel interaction is provided in a multichannel neural implant that has the ability to stimulate multiple tissue or nerve sites simultaneously. Channel interaction is minimized through measuring or estimating what the channel interaction is or will likely be, and then using that measured or estimated channel interaction to adjust the intensity of the applied stimuli so that, with the channel interaction, the actual stimuli applied to the tissue or nerves is of a desired intensity level. In one embodiment, the measured or estimated channel interaction is collected or compiled and saved as a channel interaction matrix. The channel interaction matrix is created during a fitting procedure by stimulating one channel at a time while measuring the effects of the stimulation on the neighboring channels. The superposition principal is used, as needed, to determine all the terms of the channel interaction matrix. The channel interaction matrix, once obtained, provides all of the information needed to eliminate or minimize channel interaction.

10 Claims, 10 Drawing Sheets

| DESIRED VOLTS | | CHANNEL INTERACTION MATRIX – DIAGONAL | | | | | | | | DESIRED STIMULATION CURRENT |
|---|---|---|---|---|---|---|---|---|---|---|
| V1 | = | Z1,1 | 0 | 0 | 0 | 0 | 0 | 0 | 0 | × | I1 |
| V2 | | 0 | Z2,2 | 0 | 0 | 0 | 0 | 0 | 0 | | I2 |
| V3 | | 0 | 0 | Z3,3 | 0 | 0 | 0 | 0 | 0 | | I3 |
| V4 | | 0 | 0 | 0 | Z4,4 | 0 | 0 | 0 | 0 | | I4 |
| V5 | | 0 | 0 | 0 | 0 | Z5,5 | 0 | 0 | 0 | | I5 |
| V6 | | 0 | 0 | 0 | 0 | 0 | Z6,6 | 0 | 0 | | I6 |
| V7 | | 0 | 0 | 0 | 0 | 0 | 0 | Z7,7 | 0 | | I7 |
| V8 | | 0 | 0 | 0 | 0 | 0 | 0 | 0 | Z8,8 | | I8 |

FIG. 5B $$\begin{bmatrix} Z_{1,1} & Z_{1,2} & Z_{1,3} & Z_{1,4} & Z_{1,5} & Z_{1,6} & Z_{1,7} & Z_{1,8} \\ Z_{2,1} & Z_{2,2} & Z_{2,3} & Z_{2,4} & Z_{2,5} & Z_{2,6} & Z_{2,7} & Z_{2,8} \\ Z_{3,1} & Z_{3,2} & Z_{3,3} & Z_{3,4} & Z_{3,5} & Z_{3,6} & Z_{3,7} & Z_{3,8} \\ Z_{4,1} & Z_{4,2} & Z_{4,3} & Z_{4,4} & Z_{4,5} & Z_{4,6} & Z_{4,7} & Z_{4,8} \\ Z_{5,1} & Z_{5,2} & Z_{5,3} & Z_{5,4} & Z_{5,5} & Z_{5,6} & Z_{5,7} & Z_{5,8} \\ Z_{6,1} & Z_{6,2} & Z_{6,3} & Z_{6,4} & Z_{6,5} & Z_{6,6} & Z_{6,7} & Z_{6,8} \\ Z_{7,1} & Z_{7,2} & Z_{7,3} & Z_{7,4} & Z_{7,5} & Z_{7,6} & Z_{7,7} & Z_{7,8} \\ Z_{8,1} & Z_{8,2} & Z_{8,3} & Z_{8,4} & Z_{8,5} & Z_{8,6} & Z_{8,7} & Z_{8,8} \end{bmatrix}^{-1} \times \begin{bmatrix} V_1 \\ V_2 \\ V_3 \\ V_4 \\ V_5 \\ V_6 \\ V_7 \\ V_8 \end{bmatrix} = \begin{bmatrix} I_1 \\ I_2 \\ I_3 \\ I_4 \\ I_5 \\ I_6 \\ I_7 \\ I_8 \end{bmatrix}$$

(DESIRED VOLTS) / (REQUIRED STIMULATION CURRENT)

CHANNEL INTERACTION CANCELLATION WITHIN A MULTICHANNEL NEURAL STIMULATION SYSTEM

BACKGROUND OF THE INVENTION

The present invention relates to multi-channel neural stimulators, and more particularly to a multi-channel neural stimulator that includes the ability to minimize channel interaction.

A neural stimulator provides electrical stimulation pulses to selected body tissue or nerves through one or more electrodes for the purpose of providing a desired therapeutic effect, e.g., to relive pain, to treat urinary incontinence, to aid a profoundly deaf person to hear, to treat a disease, or the like. A multichannel neural stimulator provides the capability of stimulating multiple tissue sites simultaneously with different levels of stimulation, e.g., with different current pulse amplitudes, applied to each stimulation site.

Representative neural stimulation systems are disclosed in U.S. Pat. Nos. 4,400,590; 5,324,316; 5,571,148; 5,603,726; 5,824,022; 6,308,101; and in International Publication WO 02/09808 A1, which patents and publication are incorporated herein by reference.

When multiple electrodes are stimulated simultaneously, electrical interactions can arise. See, e.g., Stickney et al., "Channel Interaction and Speech Processing Strategies for Cochlear Implants", Univ. of Texas at Dallas, House Ear Institute and Insonus Medical, Inc. Joint Presentation Report (Poster Presentation); Stickney et al. "Electrode Interaction and Speech Intelligibility in Mutlichannel Cochlear Implants", UC Irvine Department of Otolaryngology (Poster Presentation); and Boex, et al., "Electrode interactions in Clarion Subjects", University Hospitals, Geneva, Switzerland (Poster Presentation), which poster presentations are incorporated herein by reference.

It is generally known that channel interaction can be reduced by decreasing the current levels delivered to each electrode, improving electrode positioning and design, or using signal processing strategies or approaches that stimulate electrodes sequentially. The present invention provides another approach for minimizing channel interaction in a multichannel neural stimulator, such as a cochlear implant.

SUMMARY OF THE INVENTION

The present invention provides a way of reducing channel interaction in a multichannel neural implant having the ability to stimulate multiple tissue or nerve sites simultaneously.

Channel interaction is minimized, in accordance with the teachings of the present invention, through measuring or estimating what the channel interaction is or will likely be, and then using that measured or estimated channel interaction to adjust the intensity of the applied stimuli so that, with the channel interaction, the actual stimuli applied to the tissue or nerves is of a desired intensity level.

In one embodiment, the measured or estimated channel interaction is compiled and saved as a channel interaction matrix. The channel interaction matrix is created during a fitting procedure by stimulating one channel at a time while measuring the effects of the stimulation on the neighboring channels. The superposition principal is used, as needed, to determine all the terms of the channel interaction matrix.

The channel interaction matrix, once obtained, advantageously provides all of the information needed to eliminate or minimize channel interaction. In a preferred technique, this is done by using the diagonal terms of the channel interaction matrix [CIM] and a desired stimulation current matrix $[I_D]$ to compute a voltage matrix [V] that calculates what the voltage at each stimulation site would be if the desired stimulation currents were applied at each stimulation site. Then, the inverse of the channel interaction matrix, $[CIM]^{-1}$, and the voltage matrix [V] are used to determine what the required stimulation currents $[I_R]$ at each stimulation site need to be in order to produce, with the occurrence of channel interaction, the desired stimulation currents $[I_D]$.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Neural stimulation systems may take many forms. One form is a cochlear stimulation system. A cochlear stimulation system is shown, by way of example, in FIG. 1. The cochlear stimulation system includes an external speech processor portion 10 and an implantable neural stimulator (INS) portion 12. The speech processor portion 10 includes a speech processor (SP) 16 and a microphone 18. The microphone 18 may be connected directly to the SP 16, or may be coupled to the SP 16 through an appropriate communication link 24. The neural stimulation portion 12 includes an implantable neural stimulator (INS) 21, and an electrode array 48. The electrode array 48 is adapted to be inserted within the cochlea of a patient. The array 48 includes a multiplicity of electrodes, e.g., sixteen electrodes, spaced along its length that are selectively connected to the INS 21. The electrode array 48 may be substantially as shown and described in U.S. Pat. No. 4,819,647, incorporated herein by reference, or U.S. Pat. No. 6,129,753, also incorporated herein by reference. Electronic circuitry within the INS 21 allows a specified stimulation current to be applied to selected pairs or groups of the individual electrodes included within the electrode array 48 in accordance with a specified stimulation pattern, defined by the SP 16. (Here, it should be noted, that the "implantable neural stimulator" terminology is generic to any neural stimulator system. Where, as here, the nerves stimulated by the INS are auditory nerves, the INS may be referred to more particularly as an "implantable cochlear stimulator", or ICS.)

Figure 1:
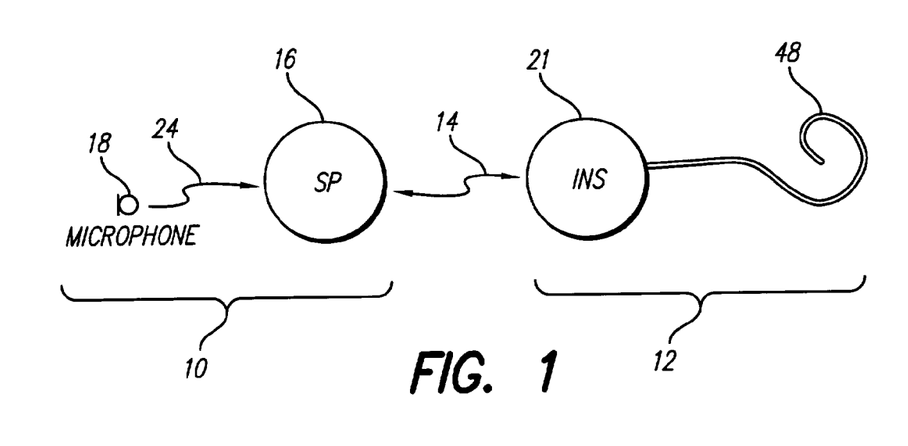
FIG. 1 shows a generalized bock diagram of a neural stimulation system, including an input transducer, a signal processor, an implantable neural stimulator and an electrode array.

The INS 21 and the SP 14 are linked together electronically through a suitable communications link 14 that allows power and control signals to be sent from the SP 16 to the INS 21, and that (in some embodiments) allows data and status signals to be sent from the INS 21 to the SP 16. The details of such communication link 14 are not important for purposes of the present invention. In some embodiments, i.e., where the INS 21 and electrode array 48 are implanted within the patient, and the SP 16 and microphone 18 are carried externally (non-implanted) by the patient, the link 14 may be realized by an antenna coil in the INS and an external antenna coil coupled to the SP. In such embodiment, i.e., when the INS has been implanted, the external antenna is positioned so as to be aligned over the location where the INS is implanted, allowing such coils to be inductively coupled to each other, thereby allowing information (e.g., the magnitude and polarity of a stimulation current) and power to be transmitted from the speech processor 16 to the INS 21. In other embodiments, i.e., where both the SP 16 and the INS 21 are implanted within the patient, the link 14 may be a direct wired connection, or other suitable link, as described, e.g., in U.S. Pat. No. 6,308,101, also incorporated herein by reference.

The microphone 18 senses acoustic signals and converts such sensed signals to corresponding electrical signals. The electrical signals are sent to the SP 16 over a suitable electrical or other link 24. The SP 16 processes these converted acoustic signals in accordance with a selected speech processing strategy in order to generate appropriate control signals for controlling the INS 21. Such control signals specify or define the polarity, magnitude, location (which electrode pair receives the stimulation current), and timing (when the stimulation current is applied to the electrode pair) of the stimulation current that is generated by the INS 21.

It is common in the cochlear stimulator art, as well as in most neural stimulation art, to condition the magnitude and polarity of the stimulation current applied to the implanted electrodes of the electrode array 48 in accordance with a specified stimulation strategy. Such stimulation strategy involves defining a pattern of stimulation waveforms that are to be applied to the electrodes as controlled electrical currents. If multiple electrode pairs exist, as is the case with a multichannel neural stimulator of the type used with the present invention, then the types of stimulation patterns applied to the multiple channels may be conveniently categorized as: (1) simultaneous stimulation patterns, and (2) non-simultaneous stimulation patterns. Simultaneous stimulation patterns may be "fully" simultaneous or partially simultaneous. A fully simultaneous stimulation pattern is one wherein stimulation currents, either analog or pulsatile, are applied to the electrodes of all of the available channels at the same time. A partially simultaneous stimulation pattern is one wherein stimulation currents, either analog or pulsatile, are applied to the electrodes of two or more channels, but not necessarily all of the channels, at the same time. Examples of each type are given below.

Analog waveforms used in analog stimulation patterns are typically reconstructed by the generation of continuous short monophasic pulses (samples). The sampling rate is selected to be fast enough to allow for proper reconstruction of the temporal details of the signal.

Current pulses applied in pulsatile stimulation patterns are generally biphasic pulses applied to the electrodes of each channel. The biphasic pulse has a magnitude (e.g., amplitude and/or duration) that varies as a function of the sensed acoustic signal. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multichannel cochlear stimulators, it is common to sample the acoustic signal at a rapid rate, and apply a biphasic stimulation pulse in sequence (i.e., non-simultaneously) to each of the pairs of electrodes of each channel in accordance with a specified pattern and cycle time, with the magnitude of the stimulation current being a function of information contained within the sensed acoustic signal at a given (e.g., the most recent) sample time. An example of such sequential, non-simultaneous stimulation pattern is a continuous interleaved sampler (CIS) strategy.

It is important to recognize that in between the two extremes of fully simultaneous stimulation patterns (wherein analog stimulation currents are continuously applied to all channels, e.g., using the Simultaneous Analog Strategy (SAS)) and non-simultaneous pulsatile patterns (wherein biphasic pules are applied in a specified sequence to all channels without time overlap, e.g., using the CIS strategy), there are a great number of other stimulation patterns may be formulated. Such other simulation patterns may prove more efficacious for a given patient than either of the SAS or CIS extremes.

It is also important to realize that the present invention finds primary applicability for use with neural stimulation systems having multiple independent current sources that can be used to independently generate the electrical stimuli applied through the electrodes of the various channels. That is, each output channel of a neural stimulator used with the present invention should be capable of being programmed to provide an electrical stimulation pattern at the same time, i.e., simultaneously with, the application of other electrical stimulation patterns to other channels. It is the presence of the simultaneous electrical stimulation patterns that gives rise to the interaction between the various channels, and it is this interaction (or the minimization of this interaction) that is the subject of the present invention.

Figure 2:
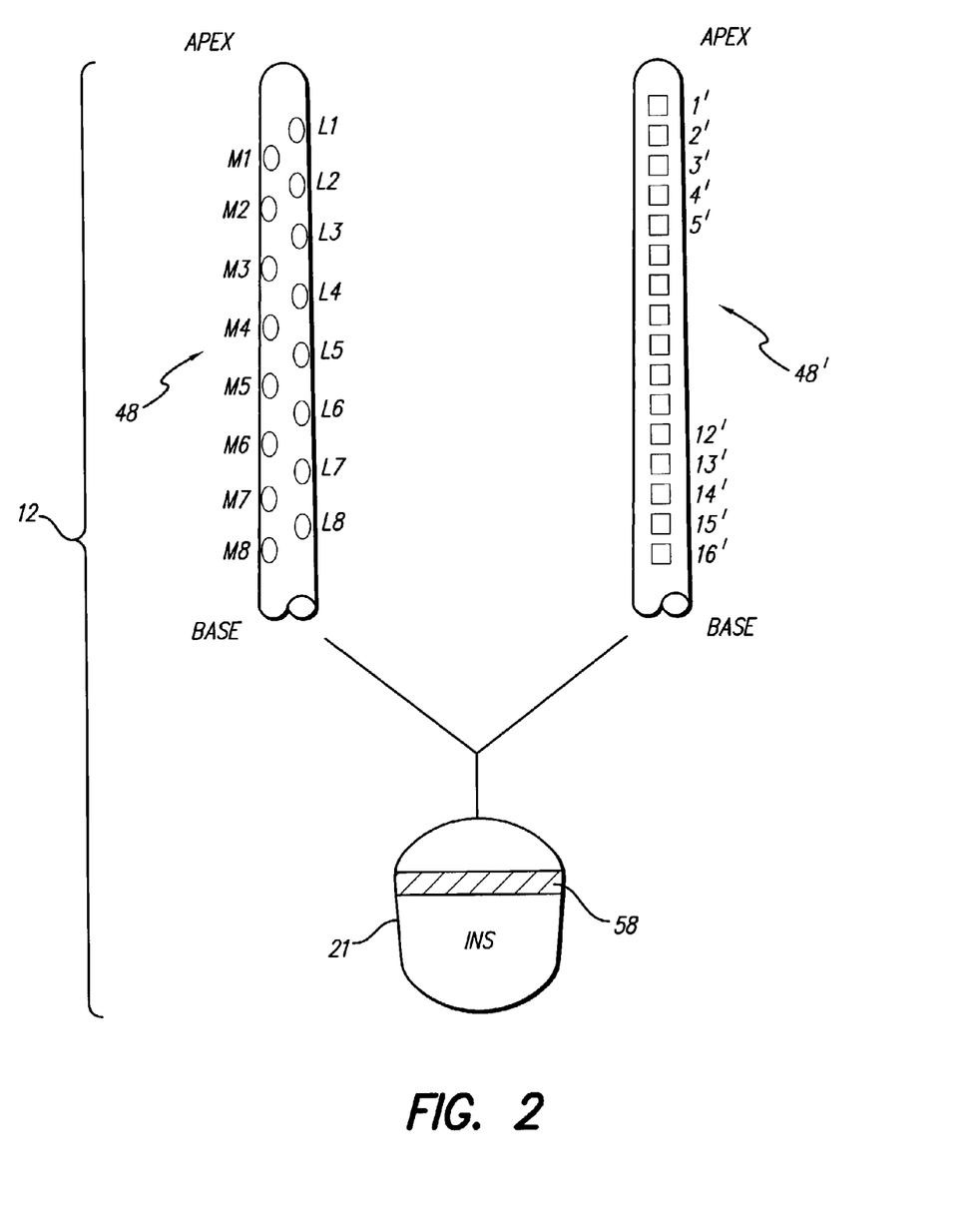
FIG. 2 schematically illustrates two types of electrode arrays that may be used with an implantable neural stimulator, whereby by way of example each electrode array has sixteen individual electrode contacts, and wherein a common or reference electrode contact is provided on the case of the implantable neural stimulator.

Turning next to FIG. 2, there is shown a schematic representation of two types of electrode arrays 48 and 48' that may be used with a neural stimulation system. Either type of electrode array 48 or 48' has its proximal end (not shown) connected to an INS 21. This connection enables the current generators within the INS for each channel to apply a current stimulus of a desired amplitude, polarity, duration and repetition rate to be applied to the paired electrode contacts for that channel.

In one embodiment, the electrode array 48 includes sixteen electrode contacts, identified in FIG. 2 as M1, L1, M2, L2, M3, L3, . . . M8, L8. As seen in FIG. 2, the electrodes identified as M1, M2, M3, . . . M8 are on the medial side of the electrode; and the electrodes L1, L2, L3, . . . L8 reside on a lateral side of the electrode. The output circuitry within the INS 21 may be configured so as to connect selected pairs of these electrodes to provide bipolar stimulation. One form of bipolar stimulation, referred to as radial bipolar, pairs electrode contacts L1 with M1, L2 with M2, and so on, through L8 with M8. Another form of bipolar stimulation, referred to as enhanced bipolar, pairs electrode contacts M1 with L2, M2 with L3, M3 with L4, M4 with L5, M5 with L6, M6 with L7, M7 with L8, and M8 with L1. Using bipolar electrode coupling, i.e., applying the stimulating electrical pulses through paired electrode contacts that are adjacent each other on the electrode array 48, provides a more focused stimulation that may be more suitable for certain types of simultaneous stimulation.

Additionally, a reference or common electrode 58 may comprise an exposed portion of a band on the case of the INS 21. Through use of such reference electrode 58, it is thus also possible to configure the system for monopolar stimulation. In monopolar stimulation, a first channel may pair electrode contact M1 or L1 with the reference electrode, a second channel may pair electrode M2 or L2 with the reference electrode, and so on, with the eighth channel pairing electrode M8 or L8 with the reference electrode. Using monopolar electrode coupling, i.e., applying the stimulating electrical pulses through paired electrode contacts that include the distant reference electrode, provides a less focused stimulation, but one which may be more suitable for other types of stimulation. Disadvantageously, monopolar stimulation also gives rise to significant channel interaction. Therefore, the present invention is particularly useful for neural stimulation systems where monopolar stimulation is employed.

Additionally, as is known in the art, virtual coupling may also be employed through appropriate mapping of the SP analysis channels with the INS stimulation channels in order to fine tune the position or location where a stimulus excites neural tissue.

Monopolar, bipolar or virtual coupling may also be used with an electrode array 48', also shown in FIG. 2. The array 48' has all of its electrode contacts along a medical side of the array. A typical bipolar coupling will pair electrodes 1 and 2, 3 and 4, 5 and 6, and so on, through 15 and 16. A typical monopolar coupling for the array 48' will pair electrodes 1, 3, 5, . . . 15 with the reference electrode 58; or electrodes 2, 4, 6, . . . 16 with the reference electrode 58.

With the foregoing as background, the main feature of the present invention—relating to the manner in which channel interaction is minimized—will next be explained in connection with the description of FIGS. 3A, 3B and 4.

Figure 3A:
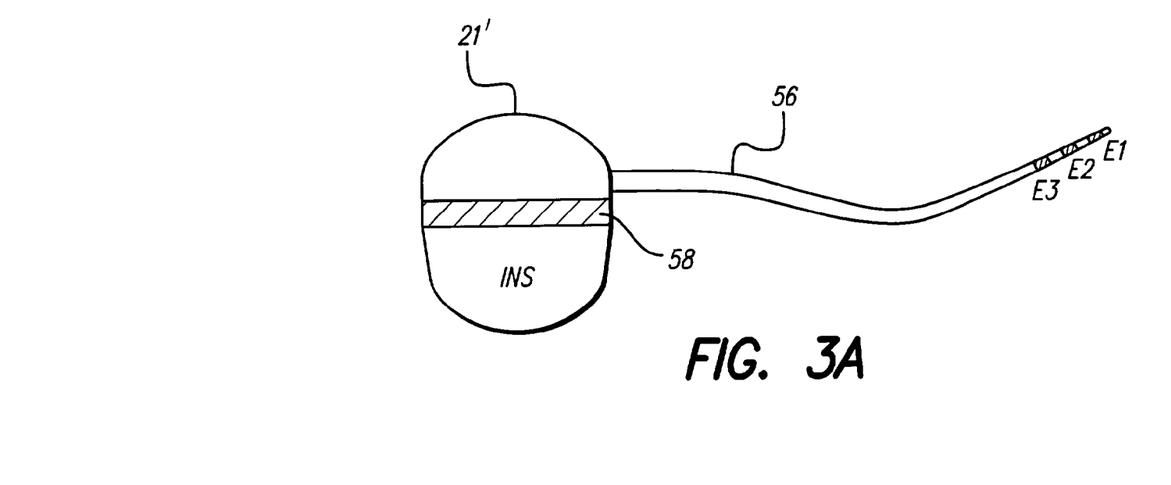
FIG. 3A shows a simplified neural stimulator having three channels through which stimulation waveforms may be applied simultaneously.
Figure 3B:
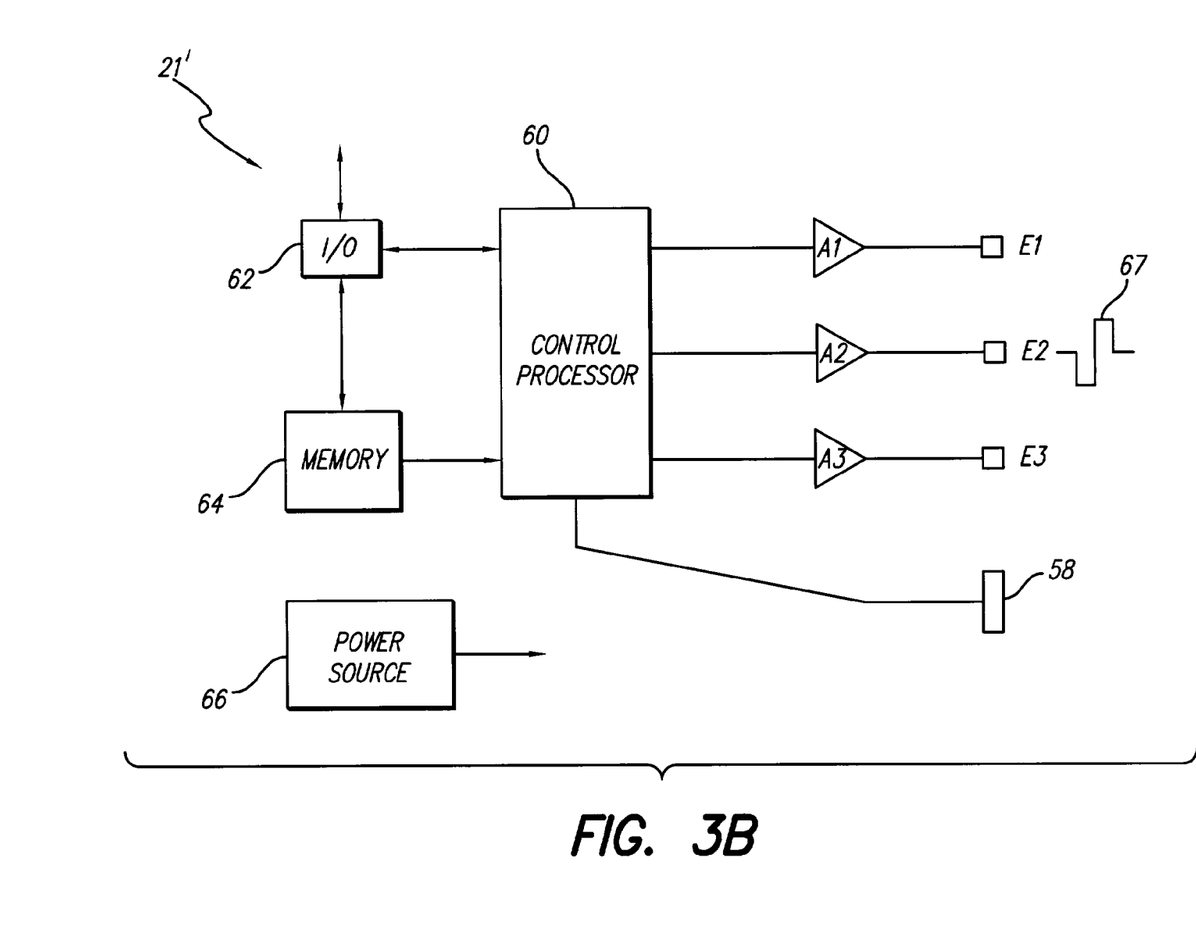
FIG. 3B shows a block diagram of the simplified neural stimulator of FIG. 3A.

FIG. 3A shows a simple implantable neural stimulator 21' having three channels. This simplified three-channel neural stimulator 21' will be used to teach the basic principles of the invention. It is to be understood however, that these same principles apply to an implantable neural stimulator (INS) having any number of channels, e.g., two to sixteen channels or more. Most multichannel nuerostimulators have at least four channels, and may have as many as thirty-two channels.

Each channel of the INS 21' is connected through suitable conductors carried in lead 56 to respective electrodes E1, E2 or E3 near the distal end of the lead 56. A functional block diagram that illustrates the circuits contained within the INS 21' is shown in FIG. 3B. As seen in FIG. 3B, each electrode E1, E2, E3 is connected to a respective current source amplifier A1, A2, or A3. These current source amplifiers A1, A2 and A3 are controlled, in turn, by a control processor 60. A reference electrode 58, e.g., an electrode located on the case of the INS 21', is also connected to the control processor 60.

The control processor 60 has suitable memory circuitry 64 connected thereto. Input/output (I/O) circuitry 62 also is coupled to the control processor 60. Such I/O circuitry 62 allows control parameters, programs, or data to be programmed into the processor 60, or into the memory 64 for use by the processor 60, so that a desired stimulation function may be carried out by the INS 21'. The I/O circuitry 62 may take many forms, as is known in the art, in order to form a transcutaneous link through which data may be sent to, or received from, the INS 21' from a location external to the INS 21'. Examples of such transcutaneous links include radio frequency (RF) links, inductive links, magnetic links, optical links, or direct wire links.

The INS 21' further includes a suitable power source 66 that provides operating power to all of its circuits, as needed. Such power source 66 may take many forms, as is known in the art, such as a primary battery, a rechargeable battery, a supercapacitor, or a power supply driven continuously by an external RF power source.

In operation, a suitable electrical stimulus is generated by one or more of the amplifiers A1, A2, or A3 as controlled by the processor 60. In FIG. 3B, a biphasic stimulus pulse 67 is shown as being present at electrode E2. A return path for such stimulus pulse 67 may be provided through electrode E1 or E3, or through the reference electrode 58.

Figure 4:
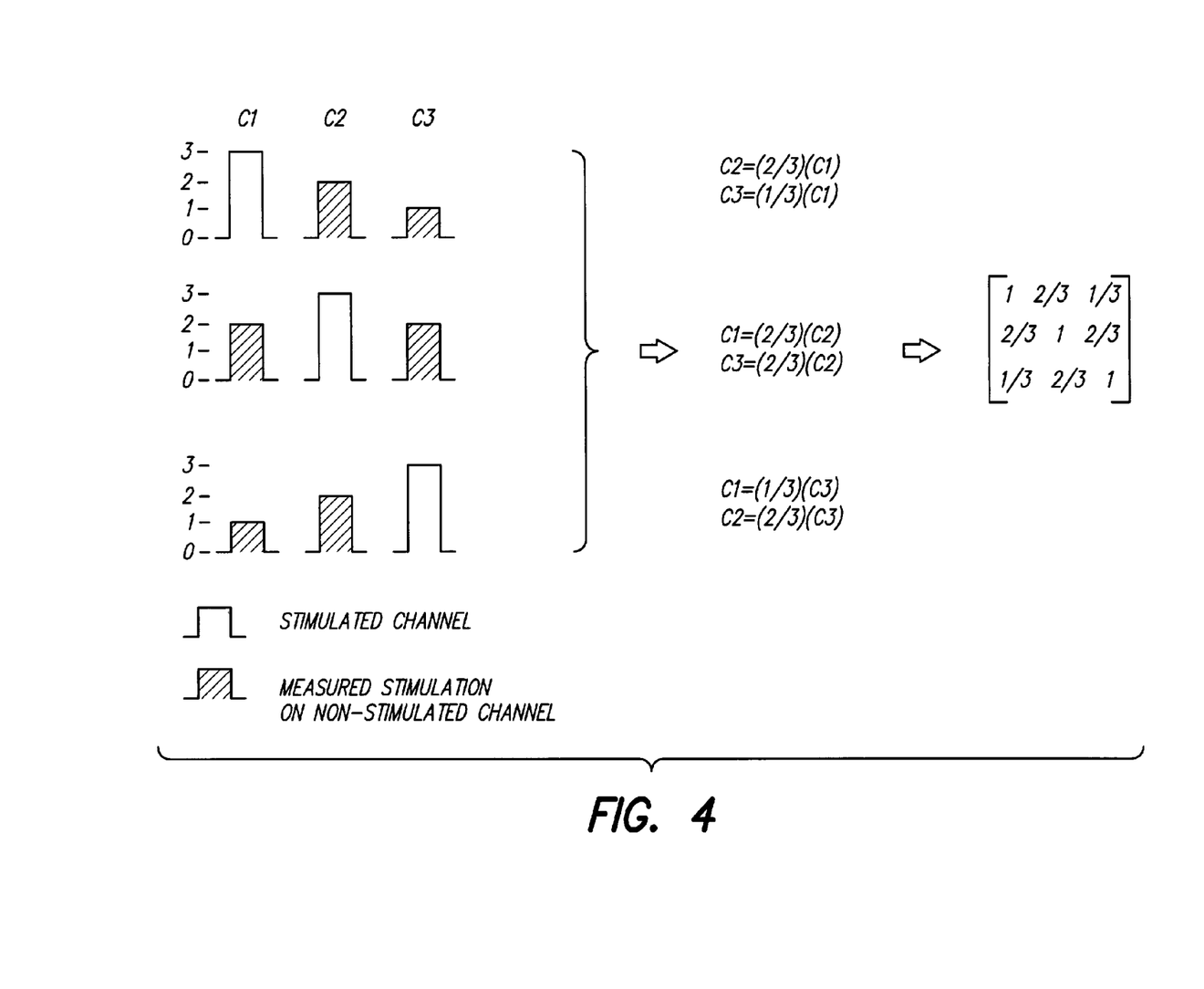
FIG. 4 illustrates the concept of channel interaction relative to the simplified neural stimulator of FIGS. 3A and 3B.

Turning next to FIG. 4, the type of channel interaction that is minimized by the present invention is illustrated. FIG. 4 assumes a three channel system, C1, C2, C3. In order to determine the channel interaction, a stimulus of a known intensity or magnitude is applied to one channel, and the interaction appearing at the other channels as a result of the application of the stimulus is measured on the other channels.

For example, assume a stimulus of intensity level 3 is applied to the first channel C1. As this stimulus is applied to C1, the magnitude of any pulses appearing on channels C2 or C3 is measured. As represented in the upper left corner of FIG. 4, a stimulus applied to C1 of intensity level 3 causes a corresponding stimulus of intensity level 2 to appear on non-stimulated channel C2, and another stimulus of intensity level 1 to appear on non-stimulated channel C3. Thus, as seen in the example of FIG. 4, a C2 stimulus equal to ⅔ of the applied stimulus C1 appears on non-stimulated channel 2 when a stimulus is applied to C1, and a C3 stimulus equal to ⅓ of the applied stimulus C1 appears on non-stimulated channel 3 when a stimulus is applied to C1. The stimulus pulses that appear on the non-stimulated channels in response to a stimulus applied to a stimulated channel represent the type of channel interaction that the present invention seeks to minimize.

Similarly, as shown in the example of FIG. 4, a stimulus applied to C2 of intensity level 3 causes a corresponding stimulus of intensity level 2 to appear on non-stimulated channel C1, and another stimulus of intensity level 2 to appear on non-stimulated channel C3. Thus, a C1 stimulus equal to ⅔ of the applied stimulus C2 appears on non-stimulated channel 1 when a stimulus is applied to C2, and a C3 stimulus equal to ⅔ of the applied stimulus C2 appears on non-stimulated channel 3 when a stimulus is applied to C2.

Likewise, a stimulus applied to C3 of intensity level 3 causes a corresponding stimulus of intensity level 1 to appear on non-stimulated channel C1, and another stimulus of intensity level 2 to appear on non-stimulated channel C2. That is to say, a C1 stimulus equal to ⅓ of the applied stimulus C3 appears on non-stimulated channel 1 when a stimulus is applied to C3, and a C2 stimulus equal to ⅔ of the applied stimulus C3 appears on non-stimulated channel 2 when a stimulus is applied to C3.

The above channel interactions can be summarized in a channel interaction matrix, or CIM, as depicted on the right side of FIG. 4. The first row of the CIM contains the channel interactions resulting from application of a stimulus to C1, the second row contains the channel interactions resulting from application of a stimulus to C2, and the third row contains the channel interactions resulting from application of a stimulus to C3, where the first column of the matrix corresponds to C1, the second column to C2, and the third column to C3.

It is the primary purpose of the present invention to minimize the channel interactions occurring on the non-stimulated channels. This is done by first stimulating each channel and collecting data from all the non-stimulated electrodes simultaneous with the applied stimulation. This data is used to build a matrix of the impedances between the stimulated electrode and the non-stimulated electrodes. This matrix of impedances comprises the channel interaction matrix, described above.

For example, consider an eight channel system. The channel interaction matrix, or CIM, is created by measuring the impedance between E1 and each of the other seven electrodes. Such impedance is preferably measured by applying a stimulus of known current I1 to electrode E1 and by measuring the resulting voltage that appears at E2, E3, E4 . . . E8. The impedance Z is simply Z=V/I, Thus, the impedance at E2 resulting from application of current I1 to E1, Z1,2, is simply $Z1,2=V2/I1$ and, in general, the impedance at any electrode Ej (j=1–8) resulting from application of a current of known magnitude to electrode Ei (I=1–8) may be expressed as $Zi,j=Vj/Ii.$ The measured impedances may be used to create an impedance matrix, or channel interaction matrix, CIM, as follows:

| Z1,1 | Z1,2 | Z1,3 | Z1,4 | Z1,5 | Z1,6 | Z1,7 | Z1,8 |
| Z2,1 | Z2,2 | Z2,3 | Z2,4 | Z2,5 | Z2,6 | Z2,7 | Z2,8 |
| Z3,1 | Z3,2 | Z3,3 | Z3,4 | Z3,5 | Z3,6 | Z3,7 | Z3,8 |
| Z4,1 | Z4,2 | Z4,3 | Z4,4 | Z4,5 | Z4,6 | Z4,7 | Z4,8 |
| Z5,1 | Z5,2 | Z5,3 | Z5,4 | Z5,5 | Z5,6 | Z5,7 | Z5,8 |
| Z6,1 | Z6,2 | Z6,3 | Z6,4 | Z6,5 | Z6,6 | Z6,7 | Z6,8 |
| Z7,1 | Z7,2 | Z7,3 | Z7,4 | Z7,5 | Z7,6 | Z7,7 | Z7,8 |
| Z8,1 | Z8,2 | Z8,3 | Z8,4 | Z8,5 | Z8,6 | Z8,7 | Z8,8 |

Figure 5A:
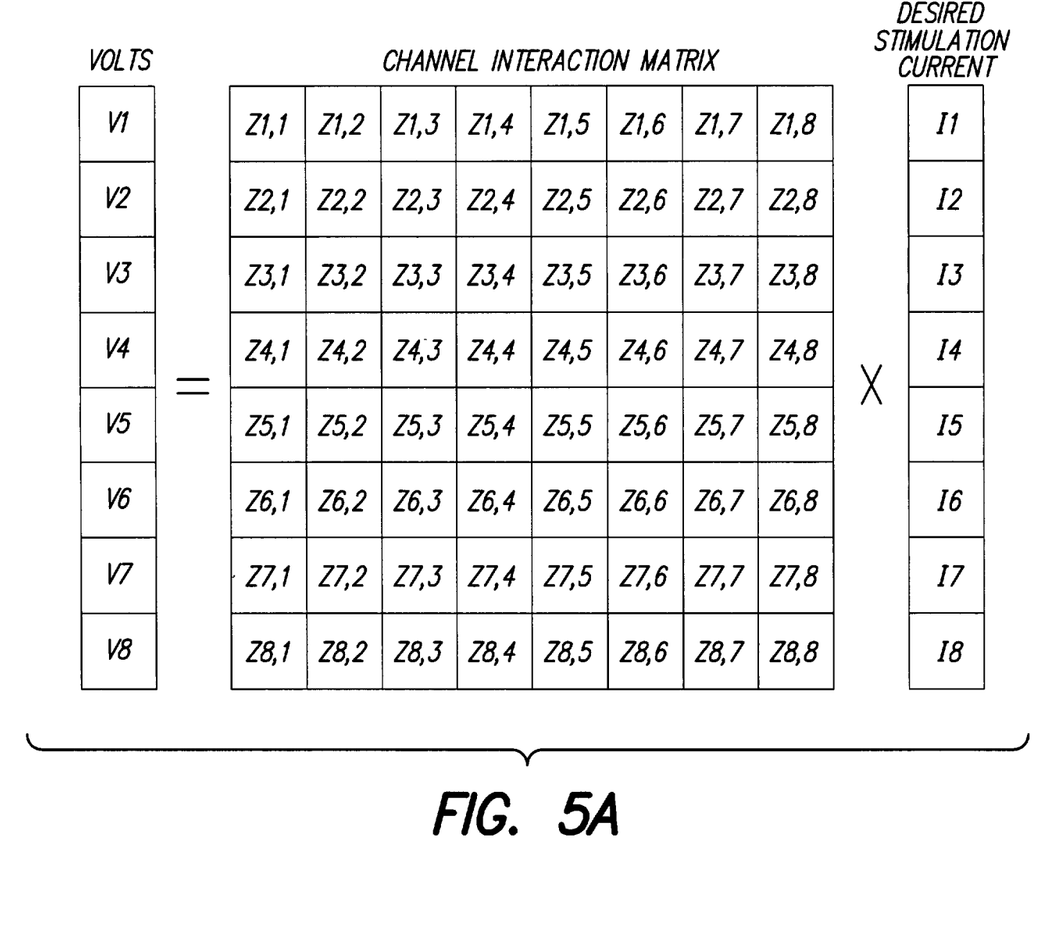
FIGS. 5A, 5B and 5C depict how the present invention uses a channel interaction matrix (CIM) to minimize channel interaction in a neural stimulation system having eight channels.

Once the impedance matrix, or channel interaction matrix (CIM) has been created, the channel interaction of the system may be modeled as shown in FIG. 5A. (Here, it should be emphasized, that while only eight channels are shown as being present in the CIM, such number is only exemplary. The principles taught herein apply to any number of channels in a multichannel neural stimulation system.)

In FIG. 5A, the desired stimulation current, I1, I2, I3, . . . I8, represents the current that the processor, or equivalent circuit, of the neural stimulation system has determined should be applied through the respective channel to the corresponding electrode E1, E2, . . . E8. However, due to channel interaction, the desired current may not be applied through the corresponding electrode because channel interaction may make the current more of less than the desired amount.

In order to assure that the correct current is applied through the corresponding electrode as determined by the processor, or equivalent circuitry, of the implantable neural stimulator, the present invention determines the voltage [V] that should appear on each electrode if the desired stimulation current $[I_D]$ were applied to the electrode. This is done by taking the diagonal terms of the CIM matrix, $[CIM_D]$, and finding the voltage [V] as follows:

$[V]=[CIM_D]\times[I_D]$

Figure 5B:
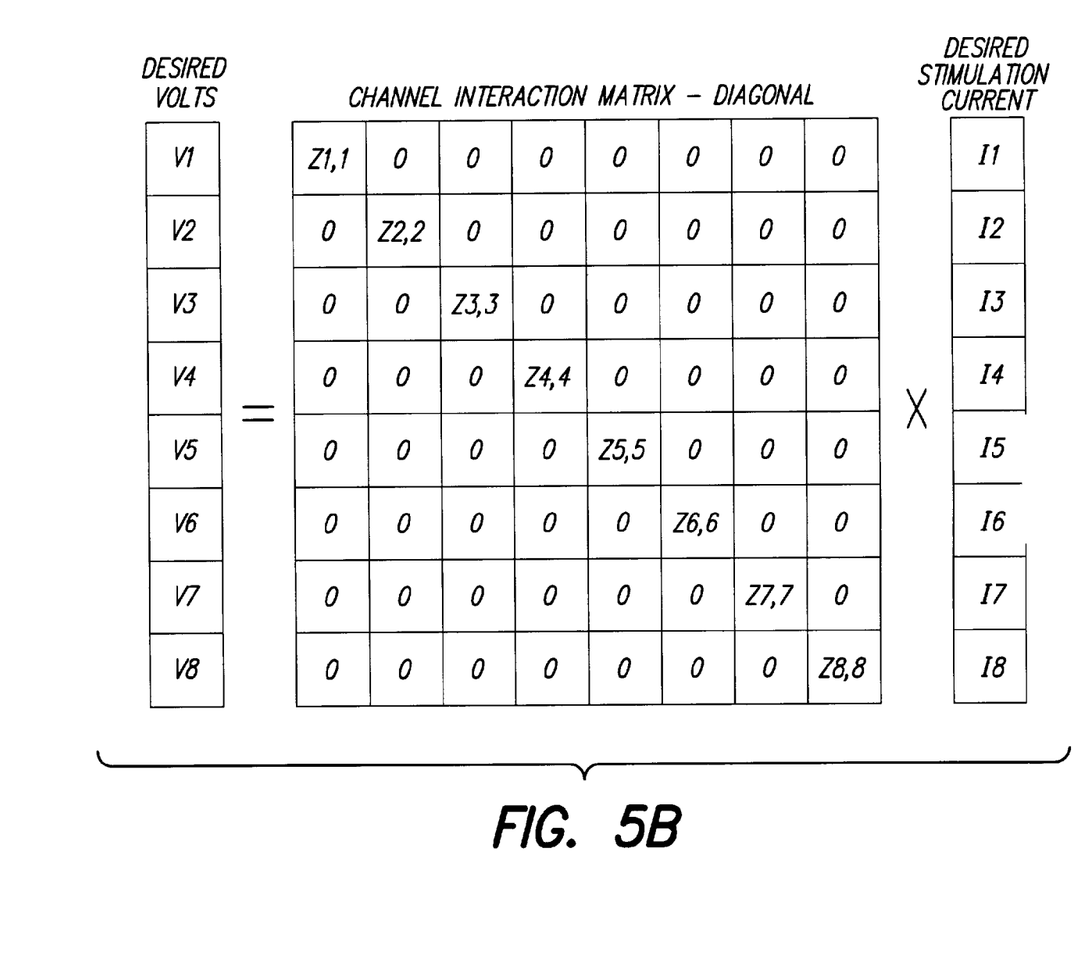

This process is also illustrated in FIG. 5B for an eight channel system.

Once the voltage [V] that should result when the correct stimulation currents are applied has been determined, as depicted above and in FIG. 5B, then the required stimulation current $[I_R]$ that will produce that voltage in the presence of the measured channel interaction is determined as follows:

$[I_R]=[CIM]^{-1}\times[V].$

Figure 5C:
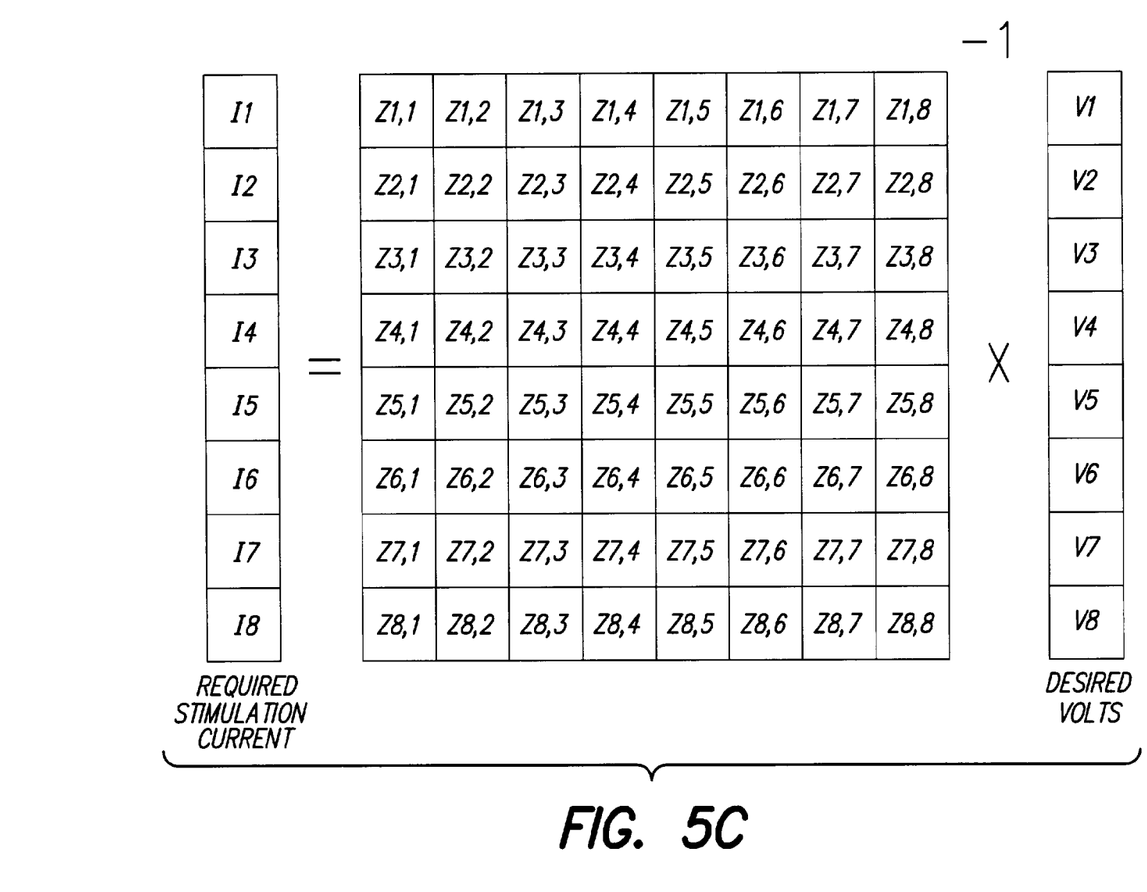

This process is illustrated in FIG. 5C for an eight channel system.

Advantageously, the channel interaction matrix [CIM] and its inverse $[CIM]^{-1}$ need only be determined once, e.g., during a fitting session. Once determined, such matrices can be saved and recalled as needed as different required stimulus currents $[I_R]$ are produced in order to respond to the demands of the implantable neural stimulator (INS) to produce a set of desired stimulation currents $[I_D]$ in order to carry out the desired function of the INS.

Further, as should be evident from the above steps, the steps may be combined in a way that eliminates the need to determine the voltage matrix [V] that should appear when the desired currents are applied through the various channels. That is, the steps represented above and in FIGS. 5B and 5C may be combined as:

$[I_R]=[CIM]^{-1}\times[V]$ where $[V]=[CIM_D]\times[I_D]$

Substituting the value of [V] into the first equation from the second equation yields:

$[I_R]=[CIM]^{-1}\times\{[CIM_D]\times[I_D]\}.$

It is thus seen that the present invention provides a method for minimizing channel interaction in a multichannel neural stimulator system, where the multichannel neural stimulation system has a multiplicity of electrodes adapted to interface with body tissue or nerves, and where means are provided for simultaneously applying a stimulus waveform of a desired intensity to selected ones of the multiplicity of electrodes. Such method comprises the steps of: (a) applying a stimulus waveform of a known intensity to one of the multiplicity of electrodes; and (b) measuring an interaction waveform appearing at any of the other of the multiplicity of electrodes as a result of the stimulus waveform applied in step (a); (c) repeating steps (a) and (b) for each of the multiplicity of electrodes; (d) creating a channel interaction matrix, [CIM], that defines the interaction waveforms measured in step (b) as a result of the stimulus waveforms, applied in step (a); (e) determining the inverse of the channel interaction matrix, $[CIM]^{-1}$, created in step (d); and thereafter (f) using the inverse of the channel interaction matrix, $[CIM]^{-1}$, and a desired stimulation waveform matrix, $[I_D]$, to determine the actual stimulation waveforms $[I_R]$ that must be applied in order to produce, after channel interaction, the desired stimulation waveforms.

Figure 6A:
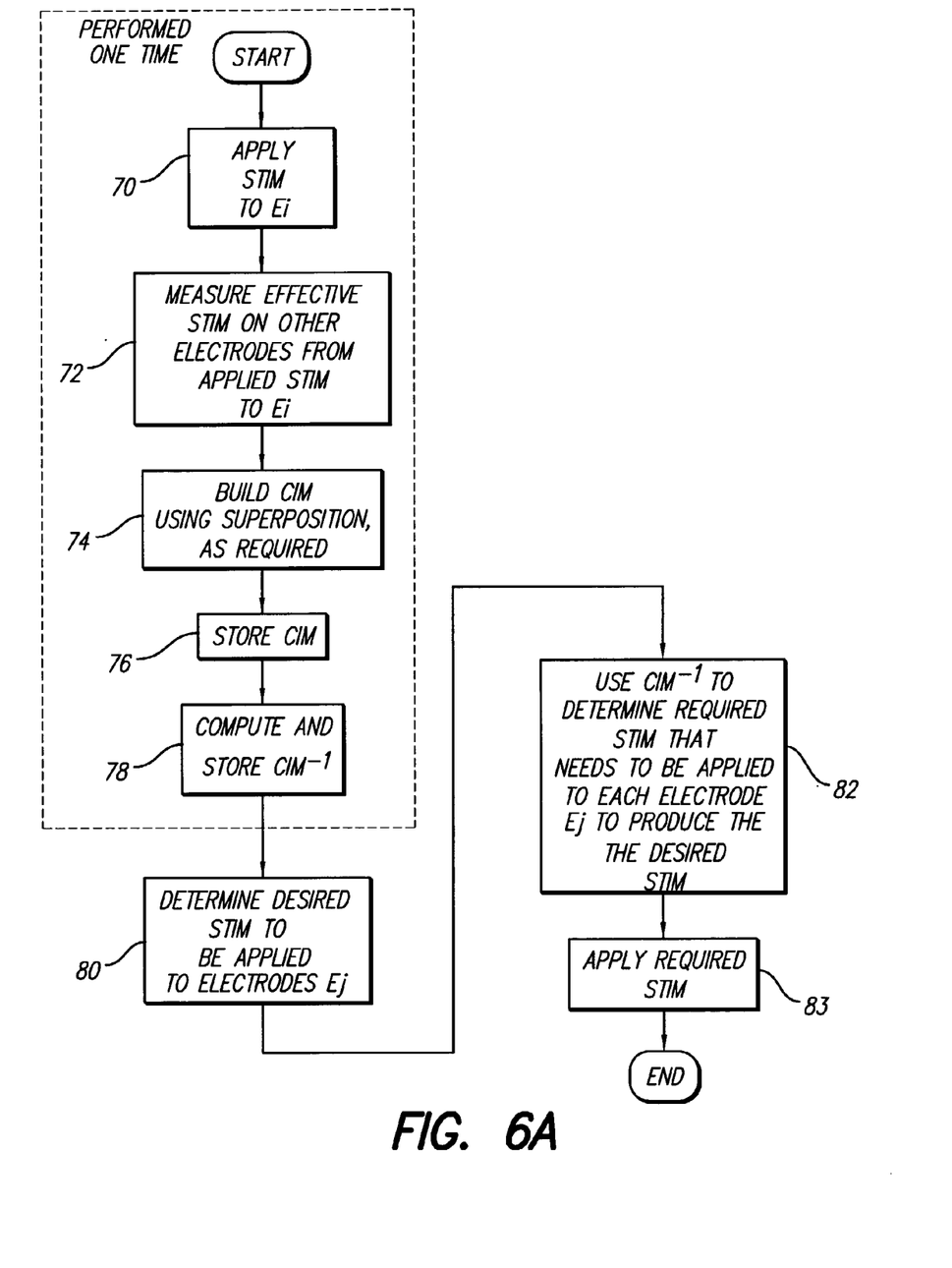
FIG. 6A is a flow chart that illustrates the main steps associated with minimizing channel interaction in accordance with the present invention.

Turning next to FIG. 6A, a flow chart is shown that summarizes the process used by the invention to minimize channel interaction. As a first portion of the process, the channel interaction matrix, or CIM (also referred to as the impedance matrix) must be created. This is done in steps (or blocks) 70-76 of FIG. 6A. In a first step, a stimulation pulse, STIM, is applied to one of the electrodes Ei (block 70). At the same time that the STIM pulse is applied to electrode Ei, the effective interaction pulse that appears on the electrodes other than Ei is measured (block 72). This process is continued so as to build the CIM (block 74), using the superposition principle as required. Once the CIM has been created, it is stored (block 76). Then, the inverse of the CIM is computed and stored (block 78). Advantageously, the steps required to build the CIM, and to compute its inverse, need only be performed once, e.g., during a fitting session.

Once the CIM has been created and stored, and its inverse has been determined and stored, such matrices may be used to minimize channel interaction as the implantable neural stimulation (INS) carries out its intended function. That is, the INS determines the desired stimulation pulses, STIM, that should be applied to each of the electrodes Ej in accordance with its intended or programmed function (block 80). The processing circuits within the INS then use the inverse of the CIM to determine the required STIM that needs to be applied to each electrode Ej to produce the desired STIM (block 82). Then the required STIM pulses are applied to the electrodes Ej through the appropriate channels of the INS (block 83).

Figure 6B:
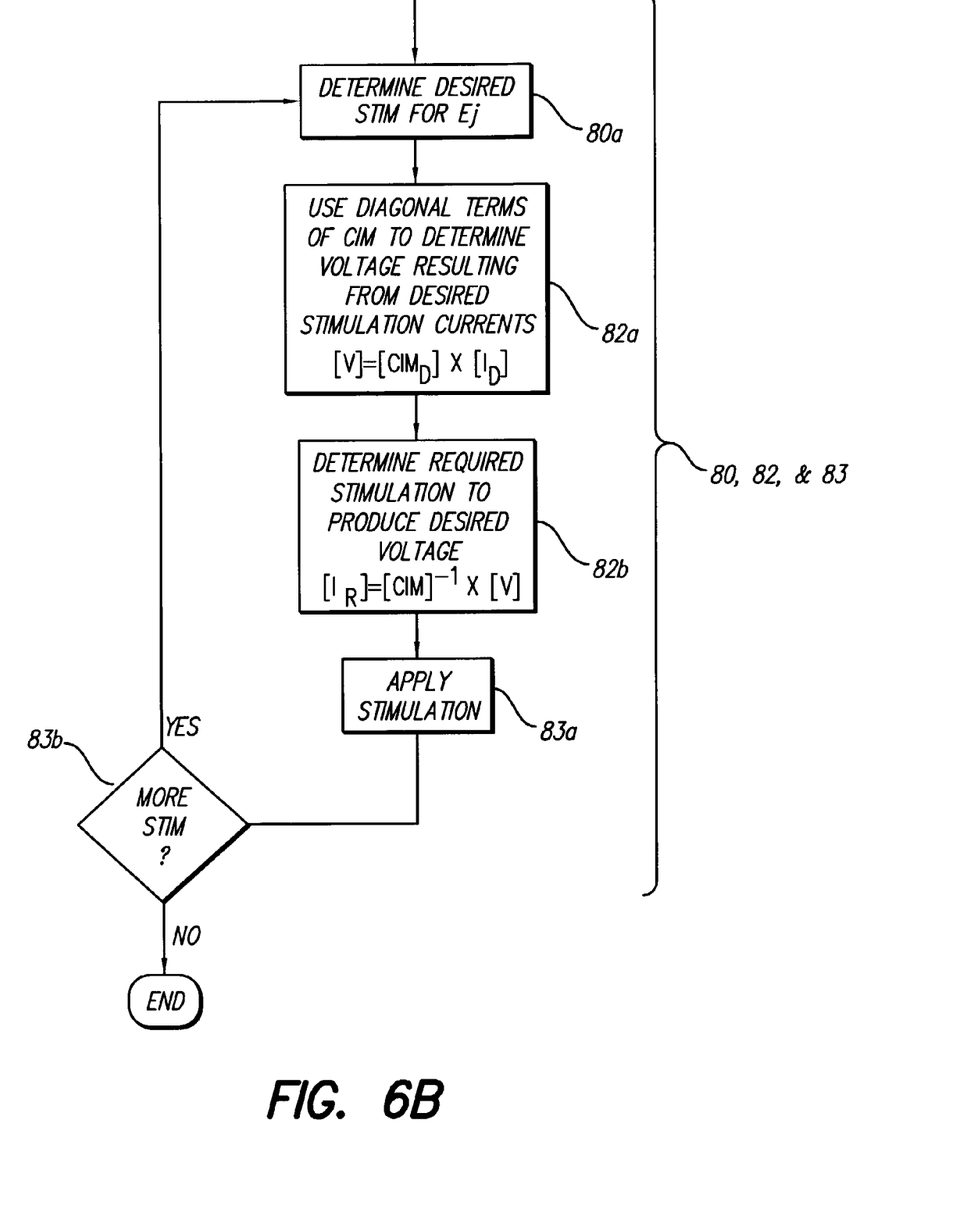
FIG. 6B details the steps that may be followed, in one embodiment, in order to carry out step 82 of the process illustrated in FIG. 6A.

A preferred manner for carrying out the steps indicated at blocks 80, 82 and 83 in FIG. 6A is depicted in more detail in FIG. 6B. This involves determining the desired stimulation currents to be applied to the electrode Ej (block 80a), and then using the diagonal terms of the CIM to determine the voltage resulting from the desired stimulation currents (block 82a). That is, $$[V]=[CIM_D]\times[I_D]$$

where [V] represents the voltage appearing on the electrodes, $[CIM_D]$ represents the diagonal terms of the channel interaction matrix, and $[I_D]$ represents the desired stimulation currents.

Once the voltage values [V] have been determined, then the required stimulation currents $[I_R]$ needed to produce those voltages are determined using the inverse of the channel interaction matrix $[CIM]^{-1}$ and the voltage values [V] (block 82b). Or, as previously indicated, $$[I_R]=[CIM]^{-1}\times[V].$$

Moreover, as previously indicated, the steps indicated at blocks 82a and 82b may be combined. That is, the required stimulation currents $[I_R]$ may be determined as follows:

$$[I_R]=[CIM]^{-1}\times\{[CIM_D]\times[I_D]\}.$$

Once the required stimulation currents have been determined (at block 82b), then those required stimulation currents are applied to the tissue (block 83a). Once applied, a determination is made as to whether the INS is to continue its operation, i.e,. whether more stimulation currents need to be applied (block 83b). If so (YES branch of block 83b), then the process repeats by completing the steps set forth at blocks 82a, 82b and 83a. If not, e.g., if the INS is to be shut down or placed in a sleep mode, or otherwise turned OFF, then the process ends (NO branch of block 83b).

Figure 7:
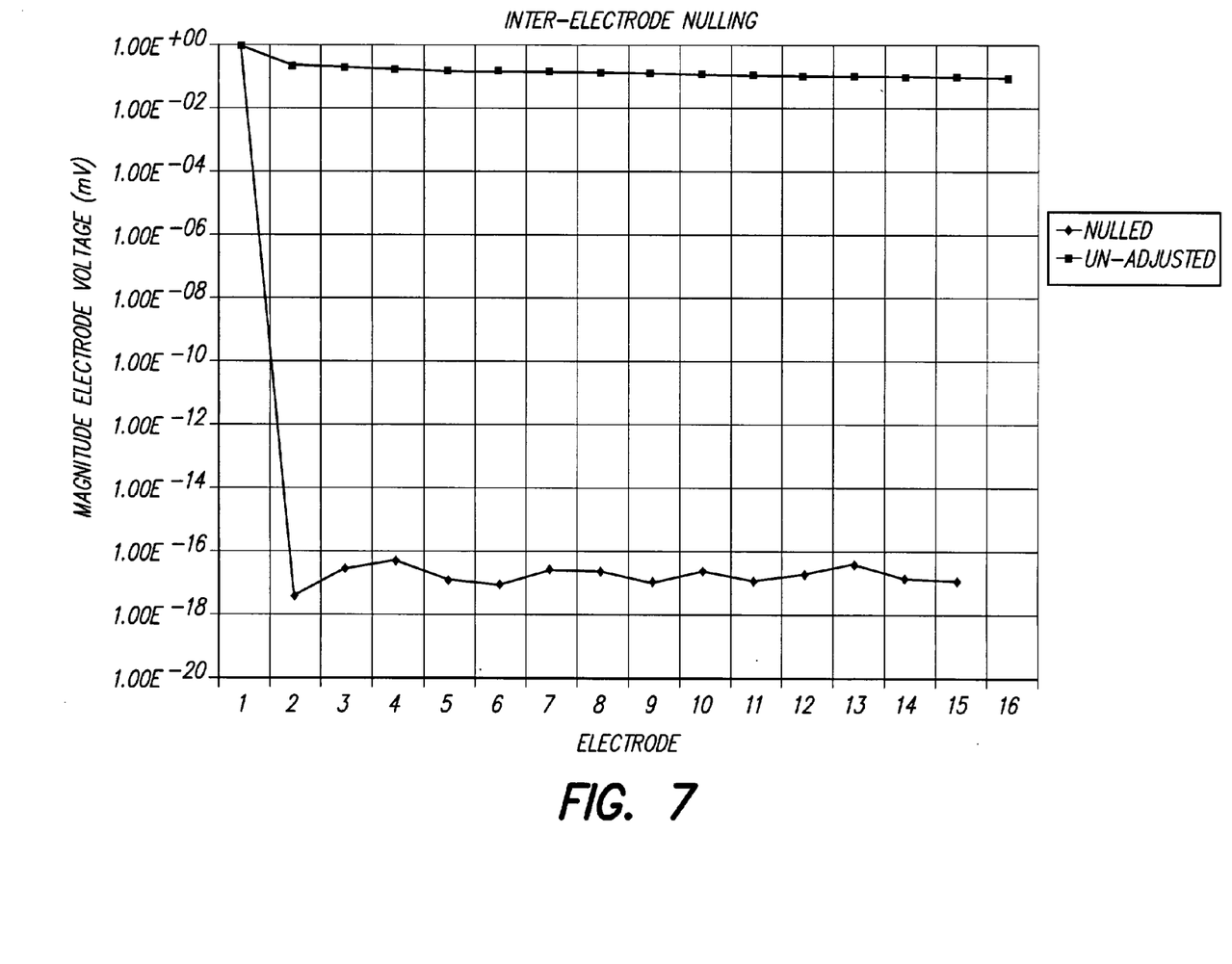
FIG. 7 is a graph depicting the inter-electrode nulling obtained using the invention.

Using the invention to minimize channel interaction has proven very effective. For example, as illustrated in FIG. 7, significant interelectrode interaction is minimized through use of the invention. FIG. 7 shows the voltages appearing on electrodes E2 through E15 of a sixteen-electrode neural stimulation system when a current stimulus is applied to electrode E1. The stimulation is carried out in a monopolar fashion relative to a reference electrode. As can be seen in FIG. 7, without using the invention ("un-adjusted" data points in FIG. 7), there is significant interaction between the 16 electrodes, with the voltage that appears on electrodes E2–E15 being only about an order of magnitude less (1.00E-01) than the stimulation value applied to electrode E1. However, when the invention is used ("nulled" data points in FIG. 7), the interaction between the 16 electrodes is effectively eliminated.

It should be appreciated that while a preferred INS configuration for practicing the invention involves applying current stimulation pulses to the electrodes, the invention may also be practiced when voltage stimulation pulses are applied to the electrodes.

While the invention herein disclosed has been described by means of specific embodiments and applications thereof, numerous modifications and variations could be made thereto by those skilled in the art without departing from the scope of the invention set forth in the claims.

What is claimed is:

1. A method for minimizing channel interaction in a multichannel neural stimulator system, said multichannel neural stimulation system having a multiplicity of electrodes adapted to interface with body tissue or nerves, and means for simultaneously applying a stimulus waveform of a desired intensity to selected ones of the multiplicity of electrodes, the method comprising:
   (a) applying a stimulus waveform of a known intensity to one of the multiplicity of electrodes; and
   (b) measuring an interaction waveform appearing at any of the other of the multiplicity of electrodes as a result of the stimulus waveform applied in step (a);
   (c) repeating steps (a) and (b) for each of the multiplicity of electrodes;
   (d) creating a channel interaction matrix, [CIM], that defines the interaction waveforms measured in step (b) as a result of the stimulus waveforms, applied in step (a);
   (e) determining the inverse of the channel interaction matrix, $[CIM]^{-1}$, created in step (d); and thereafter
   (f) using the inverse of the channel interaction matrix, $[CIM]^{-1}$, and a desired stimulation waveform matrix, $[I_D]$, to determine the actual stimulation waveforms $[I_R]$ that must be applied in order to produce, after channel interaction, the desired stimulation waveforms.

2. The method of claim 1 wherein step (f) comprises determining the voltage [V] resulting from application of the desired stimulation waveforms, $[I_D]$, using the diagonal terms of the channel interaction matrix, $[CIM_D]$, as:

$$[V]=[CIM_D]\times[I_D];\text{ and}$$

determining the required stimulation waveforms $[I_R]$ needed to produce the voltage [V] in the presence of channel interaction as:

$$[I_R]=[CIM]^{-1}\times[V].$$

3. The method of claim 1 wherein step (f) comprises determining the required stimulation waveforms $[I_R]$ needed to produce the desired stimulation waveforms, $[I_D]$, in the presence of channel interaction as:

$$[I_R]=[CIM]^{-1}\times\{[CIM_D]\times[I_D]\}.$$

4. A method of reducing channel interaction in a multichannel neural implant having the ability to stimulate multiple tissue or nerve sites simultaneously, comprising:
   stimulating one channel at a time;
   measuring the effects of the stimulation on neighboring channels;
   estimating what the channel interaction will likely be responsive to said measuring step, and
   using the estimated channel interaction to adjust the intensity of the applied stimuli so that, with the channel interaction, the actual stimuli applied to the tissue or nerves is of a desired intensity level.

5. The method of claim 4 further comprising building a channel interaction matrix that defines the effects of the stimulation on neighboring channels when stimulation is applied to one channel at a time.

6. The method of claim 5 wherein using the estimated channel interaction to adjust the intensity of the applied stimuli comprises determining the inverse of the channel interaction matrix and multiplying the inverse of the channel interaction matrix by the desired stimulation to determine the adjusted intensity of the applied stimuli.

7. A multichannel neural stimulation system comprising:
   a multiplicity of electrodes adapted to interface with body tissue or nerves;
   means for simultaneously applying a stimulus waveform of a desired intensity to selected ones of the multiplicity of electrodes;
   means for creating a channel interaction matrix [CIM] that defines inter-electrode interaction resulting when a stimulus waveform is applied to one electrode and causes a stimulus waveform to appear on non-stimulated electrodes;
   means for determining the inverse of the channel interaction matrix, $[CIM]^{-1}$;
   means for using the inverse of the channel interaction matrix, $[CIM]^{-1}$, and a desired stimulation waveform matrix, $[I_D]$, to determine the actual stimulation waveforms $[I_R]$ that must be applied in order to produce, after channel interaction, the desired stimulation waveforms.

8. The multichannel neural stimulation system of claim 7 wherein the means for determining the channel interaction matrix [CIM] comprises
   means for applying a stimulus waveform of a known intensity to each of the multiplicity of electrodes, in turn; and
   means for measuring an interaction waveform appearing at any of the other of the multiplicity of electrodes as a result of the applied stimulus waveform to one of the multiplicity of electrodes.

9. The multichannel neural stimulation system of claim 8 wherein the means for using the inverse of the channel interaction matrix, $[CIM]^{-1}$, and a desired stimulation waveform matrix, $[I_D]$, to determine the actual stimulation waveforms $[I_R]$ that must be applied in order to produce, after channel interaction, the desired stimulation waveforms comprises:
   means for determining the voltage [V] resulting from application of the desired stimulation waveforms, $[I_D]$, using the diagonal terms of the channel interaction matrix, $[CIM_D]$, as:

$$[V]=[CIM_D]\times[I_D];\text{ and}$$

means for determining the required stimulation waveforms $[I_R]$ needed to produce the voltage [V] in the presence of channel interaction as:

$$[I_R]=[CIM]^{-1}\times[V].$$

10. The multichannel neural stimulation system of claim 8 wherein the means for using the inverse of the channel interaction matrix, $[CIM]^{-1}$, and a desired stimulation waveform matrix, $[I_D]$ to determine the actual stimulation waveforms $[I_R]$ that must be applied in order to produce, after channel interaction, the desired stimulation waveforms comprises means for determining the required stimulation waveforms $[I_R]$ needed to produce the desired stimulation waveforms, $[I_D]$, in the presence of channel interaction as:

$$[I_R]=[CIM]^{-1}\times\{[CIM_D]\times[I_D]\}$$

where $[CIM_D]$ comprises a matrix made up of the diagonal terms of the channel interaction matrix [CIM].

* * * * *